United States Patent

Stark et al.

[11] Patent Number: 6,024,709
[45] Date of Patent: Feb. 15, 2000

[54] URINE SPECIMEN CUP ARRANGEMENT

[76] Inventors: Wayne T. Stark, 4787 Yorkshire Way, Granite Bay, Calif. 95746; Raymond J. Mikelionios, 203 Grove St., Roseville, Calif. 95678

[21] Appl. No.: 08/925,397

[22] Filed: Sep. 8, 1997

[51] Int. Cl.[7] ........................................ A61B 5/00
[52] U.S. Cl. .................. 600/573; 604/317; 220/359.3
[58] Field of Search ............................. 600/573; 604/317, 604/404; 422/102; 220/214, 359.1–359.5, 361

[56] References Cited

U.S. PATENT DOCUMENTS

| | | | |
|---|---|---|---|
| 3,432,087 | 3/1969 | Costello . | |
| 3,777,739 | 12/1973 | Raitto | 604/317 |
| 3,881,465 | 5/1975 | Raitto | 128/2 F |
| 4,064,760 | 12/1977 | Benjamin | 73/421 R |
| 4,244,920 | 1/1981 | Manschot et al. | 604/317 |
| 4,315,047 | 2/1982 | Seabold et al. | 428/64 |
| 4,409,989 | 10/1983 | Larribas | 128/760 |
| 4,630,761 | 12/1986 | Thomson | 600/573 |
| 4,735,335 | 4/1988 | Torterotot | 220/270 |
| 5,329,644 | 7/1994 | Scott | 4/144.2 |
| 5,579,943 | 12/1996 | Johnson | 220/258 |

*Primary Examiner*—Max Hindenburg
*Attorney, Agent, or Firm*—Don B. Finkelstein

[57] ABSTRACT

A urine specimen cup with a cup portion and a lid portion mountable on the cup portion in a sealing relationship. The lid portion has walls defining an aperture therethrough and a flexible tab is mounted on the lid portion to cover the aperture and also extend over the rim of the lid portion to engage the cup portion. The first section of the tab which overlies the aperture is provided with a resealable adhesive to allow repeated lifting of the first section to provide access to the urine specimen in the cup and then be resealed. The second section of the tab has a permanent adhesive so that once adhered it provides a permanent seal between the cup and lid to insure integrity of the sample. A tear line is provided between the first and second sections of the tab to allow ultimate removal of the lid from the cup for disposal of the specimen.

13 Claims, 1 Drawing Sheet

URINE SPECIMEN CUP ARRANGEMENT

BACKGROUND OF THE INVENTION

1. Field of the Invention

This invention relates to the sealable container art and more particularly to a sealable urine specimen cup.

2. Description of the Prior Art

The collection of urine for examination and testing for the presence of chemicals which may be in the urine is a standard medical procedure utilized in medical examinations for a variety of purposes and in a variety of fields. One of the fields in which the use of testing urine specimens has increased is in the sports and related fields wherein athletes are often required to provide urine specimens for testing so that the presence of prohibited substances may be detected. In certain sporting events such as the Olympic Games, a vast number of urine specimens are collected and tested for the many athletes competing therein. In such events as well as in other sports related testing of urine specimens, it is imperative that the integrity of the specimen, once collected, be maintained so that there is no opportunity for a misidentification of the person providing the urine specimen or the contamination of the sample during the testing process.

Since during the testing process it is often required that portions of the urine specimen be removed from the specimen cup over a period of time, it is necessary to provide a urine specimen cup wherein small portions of the urine sample in the cup may be removed at various times but the contents of the cup between the times of sample removal be maintained in a sealed condition to prevent contamination and also that the specimen cup itself have a positive indication that the contents of the cup have not been tampered with or changed. Further, it is often been shown to be required that a portion of the urine in the original specimen cup be maintained so that further testing of the specimen in the event of a challenge to the accuracy of the first tests may be done.

Typical urine specimen cups generally include a liquid containing cup portion and a removable lid for the cup portion. After the urine is placed in the cup portion, the lid is connected thereto, usually by a conventional threading engagement, a snap on engagement or other engagement devices which provide a sealed specimen cup once the lid is installed. When it is desirable to remove a small portion of the urine for the various tests, in many prior art specimen cups the entire lid was removed and the desired amount of urine is removed from the cup portion and the lid then reinstalled. In other tests, various testing probes are inserted into the urine in the cup to determine the reaction of the urine to the particular test probe. Such arrangements have often led to either contamination of the specimen or charges that, once the cup was at the testing facility, the contents were changed or the sample mixed or contaminated. Further, the integrity of any portion of the urine specimen left after the first testings was called into question since it was not heretofore possible to provide an insurance that the lid had not been removed and the contents contaminated or otherwise not as originally contained in the specimen cup.

Also, in many prior art urine specimen cup arrangements, the entire lid of the cup had to be removed completely before access to the urine sample contained therein could be achieved. In such arrangements, it has often been found that the urine in the cup had splashed onto the inside of the lid of the cup and when the lid was removed, the urine from the lid spilled or splashed onto the person removing the lid. Therefore, protection of the person performing the tests from urine spills as well as maintaining the integrity if the urine specimen and preserving the integrity of the specimen in the cup after the conclusion of the testing are desiderata sought in the medical profession.

Thus, it has long been desired that there be provided a urine specimen cup from which the small amounts required for testing may be withdrawn or otherwise used at various times, that the specimen cup be sealed between each instance of removal or use of the small test samples from the cup, and that an indication be provided at all times after the sample of urine is placed in the cup that the lid has not been removed so the integrity of the sample remaining in the cup cannot be questioned. It is also desired that the person withdrawing the urine from the cup or otherwise using the urine in the cup for testing be protected from spills or splashes of the urine.

SUMMARY OF THE INVENTION

Accordingly, it is an object of the present invention to provide an improved urine specimen cup.

It is another object of the present invention to provide an improved urine specimen cup from which test samples may be withdrawn or otherwise tested at various times and the cup remains sealed between times that urine is withdrawn.

It is another object of the present invention to provide a urine specimen cup having a seal arrangement that indicates if the cup has been opened by removing the lid thereof after the sample of urine has been initially placed therein.

It is still a further object of the present invention to provide an improved urine specimen cup in which testing of urine samples does not result in the person performing the tests being subjected to spills or splashes of the urine.

The above, and other objects of the present invention are achieved, according to a preferred embodiment thereof, in a urine specimen cup arrangement having a cup portion in which the urine specimen to be tested is initially place. The shape of the cup portion may be as desired for particular applications as long as it has the characteristics for accepting a lid portion as described herein. The cup portion has an open end and the urine sample to be tested is placed in the cup through the open end thereof. A lid portion is provided which engages the open end of the cup portion in a sealing relationship. Such sealing relationship may be achieved by, for example, a screw thread engagement therebetween, a press seal wherein the cup portion is rigid and the lid portion has a preselected resiliency to slip over a sealing rim on the cup portion, or any other desired sealing arrangement. The lid portion has a top section that overlies the open end of the cup and a rim section extending around the cup portion in regions adjacent the open end of the cup portion. The top section of the lid portion has walls defining a small aperture therein preferably located in regions adjacent the rim section for purposes as hereinafter set forth.

In the present invention, the urine to be tested is accessed through the aperture without requiring that the lid portion be removed from the cup portion. In order to achieve this goal, a flexible tab is provided to cover the aperture and the flexible tab has a first portion for covering the aperture and a second portion extending over the rim and engaging both the rim and the cup portion. The first portion of the flexible tab has a resealable adhesive on the underside thereof so that the first potion of the flexible tab may be lifted from the lid to allow urine in the cup portion to be accessed and then the flexible tab replaced to cover and seal the aperture between times that urine is being accessed for testing. The second portion of the flexible tab has a first section that is sealed to the rim section of the lid portion and also to the cup portion in regions adjacent the rim section. The glue or other adhesive on the second portion of the flexible tab provides a permanent seal between the lid portion and the cup portion. A tear line is provided on the flexible tab to divide the flexible tab between the first section and the second section thereof.

In use, after the urine is placed in the cup portion, the lid portion is attached thereto. The flexible tab, which may be separate from the lid portion or detachably attached to the lid portion for detachably sealing the aperture in the lid portion, is applied so that the first section of the flexible tab detachably covers the aperture and then the second portion of the flexible tab is pressed into sealing engagement with the rim portion and the cup portion. The urine specimen cup is then, generally, transported to the facility wherein the testing of the urine may be accomplished. When the first sample of the urine is to be removed for testing, the flexible tab is severed at the tear line and the first section of the flexible tab is lifted form the lid to open the aperture and allow the urine sample that is to be tested to be accessed for testing through the aperture. After the first test on the urine sample is accomplished, the first section of the flexible tab is replaced over the aperture to reseal the aperture. The first section of the flexible tab may be repeatedly removed and replaced as additional urine samples are accessed in the cup portion through the aperture.

The second section of the flexible tab remains in place and in sealing engagement with both the rim section of the lid portion and the cup portion. The second section of the flexible tab thus provides an indication that the lid portion of the urine specimen cup has not been removed from the cup portion. To provide further insurance of the integrity of the urine specimen cup after the urine to be tested is placed therein, a seal overlying the second portion of the flexible tab and engaging the cup portion may be used, a stamped seal in such location may be used, or other structures as desired may be incorporated for the purpose.

By providing the small aperture in the rim for access to the urine for testing, the entire rim does no need to be removed. This minimizes the chance of urine spilling or splashing onto the person doing the testing. Therefore, even in those applications where long term integrity of the urine remaining in the cup at the conclusion of all tests is not an absolute requirement, the present invention has utility in minimizing the spilling or splashing of urine during the testing operations.

BRIEF DESCRIPTION OF THE DRAWING

The above and other objects of the present invention may be more fully understood from the following detailed description taken together with the accompanying drawing wherein similar reference characters refer to similar elements throughout and in which.

DESCRIPTION OF THE PREFERRED EMBODIMENTS

Figure 1:
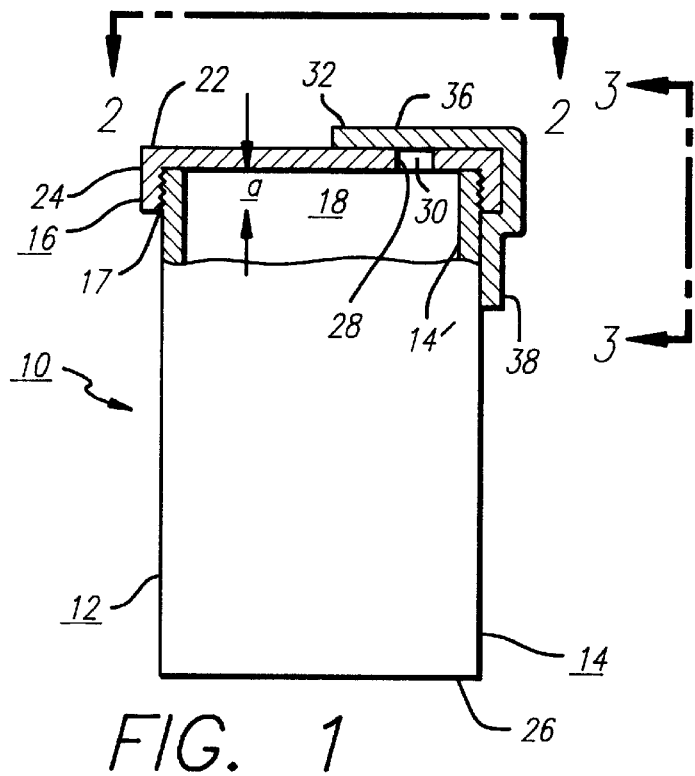
FIG. 1 illustrates a preferred embodiment, partially in section, according to the principles of the present invention of an improved urine specimen cup in a sealed condition.

Referring now to the drawing, there is illustrated a preferred embodiment generally designated 10 of an improved urine specimen cup generally designated 12 according to the principles of the present invention. The urine specimen cup 12 has a cup portion 14 and a lid portion 16 which sealingly engages the cup portion at the top thereof as indicated at 17. The lid portion 16 sealingly closes the open top 18 of the cup portion 14 for the condition of the lid portion 16 of the cup 12 installed thereon. The lid portion 16 has a top section 22 and a rim section 24. The top section 22 overlies the open top 18 of the cup portion 14 and the rim section 24 encloses the top 18 of the cup portion 14 and extends towards the bottom 26 of the cup portion 14 a preselected distance indicated by the letter "a".

As shown on FIG. 1, the lid portion 16 threadingly engages the cup portion 14 as indicated at 17 to provide a seal therebetween. Other types of engagement between the lid portion 16 and the cup portion 14 may be utilized as desired and such are well known in the art as used, for example, in various food containing jars and the like. The lid portion 16 has walls 28 defining an aperture 30 therethrough. The aperture 30 is, in preferred embodiments of the present invention, in regions adjacent the rim section 24 but preferably spaced from the side walls 14' of the cup portion 14.

A flexible seal 32 is provided in the embodiment 10 for both a repetitive detachable sealing to the lid portion 16 in regions adjacent the aperture 30 as well as, in those embodiments of the present invention requiring it, a positive indication that the lid portion 16 has not been removed from the cup portion 14.

Figure 4:
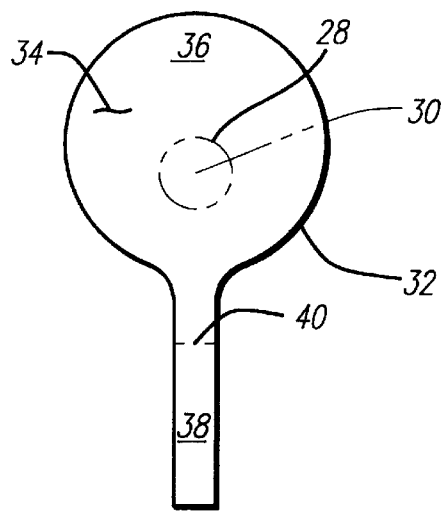

FIG. 4 illustrates the flexible seal 32 in a plan view thereof to illustrate the details thereof. The flexible seal 32 has an underside 34 upon which the adhesives required herein are placed. The flexible seal 32 is fabricated from a comparatively thin plastic sheet, such as a vinyl having a thickness on the order of about 0.1 mm to 0.4 mm though thicker or thinner sheets may be utilized and materials other than vinyl may be utilized as desired for particular applications. The flexible tab 30 has a first section 36 upon which a pressure sensitive detachably adhering adhesive coating is applied. The first section 36 is positioned to cover the aperture 30, shown in phantom lines on FIG. 4, for the condition of the flexible tab 32 is installed on the lid portion 16 of the specimen cup 12 to provide a detachable sealing of the aperture 30. The flexible tab 32 also has a second section 38 which overlies both a portion of the rim section 24 of the lid portion 16 as well as a part of the cup portion 14. In those embodiments of the present invention wherein a positive indication that the lid portion 16 has not been removed from the cup portion 14, the second section 38 is provided with a non detachable pressure sensitive adhesive coating. A tear line indicated at 40 is provided to allow separation of the first section 36 from the second section 38 when it is desired to access the contents of the specimen cup 12 through the aperture 30. In other embodiments of the present invention wherein it is not required to have a positive indication that the lid portion 16 has not been removed from the cup portion 14, the second section 38 of the flexible tab 32 may be provided with the same pressure sensitive detachable adhesive coating as applied to the first section 36.

Figure 1A:
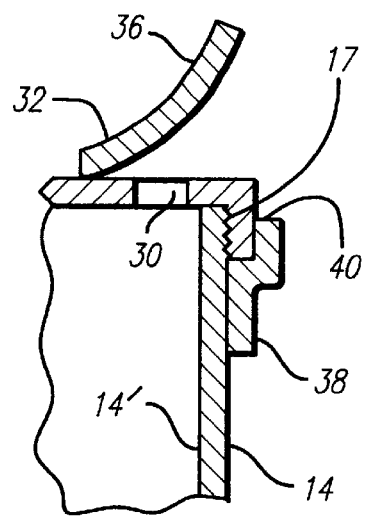
FIG. 1A illustrates the embodiment shown in FIG. 1 with the contents of the urine specimen cup are accessible.
Figure 2:
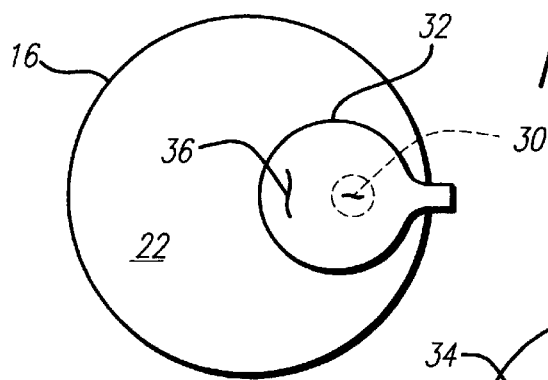
FIG. 2 is a top view of the embodiment shown in FIG. 1 taken along the line 2—2 of FIG. 1.

In use, after the urine specimen to be tested has been placed in the urine specimen cup 12 the lid portion 16 is placed on the cup portion 14 . The first section 36 of the flexible tab 32 is then applied to the top section 22 of the lid portion 16 in regions adjacent the aperture 30 to provide a seal of the aperture 30. The second section 38 of the the flexible tab 32 is pressed against the rim section 24 of the top portion 16 and the adjacent part of the side wall 14' of the cup portion 14 as indicated at 14". The urine specimen cup may then be transported to the one or more facilities where the testing of the urine sample is to be performed. When it is desired to access the urine contained in the cup portion 14, the flexible tab 32 may be severed at the tear line 40 and the first section 36 lifted to allow access to the contents of the cup portion 14 through the aperture 30 as illustrated in FIG. 1A. When the access to the contents is no longer necessary for the test being performed, the first section 36 is pressed back into place over the aperture 30 to provide the sealing thereof. This process may be repeated as many times as necessary for the various sequential tests of the urine sample contained in the cup 12 as desired. Since the lids portion 16 is not removed during any of the testing performed on the urine specimen, the splashing or spilling of the urine which may be on the lid 16 onto the person performing the tests is minimized.

Figure 3:
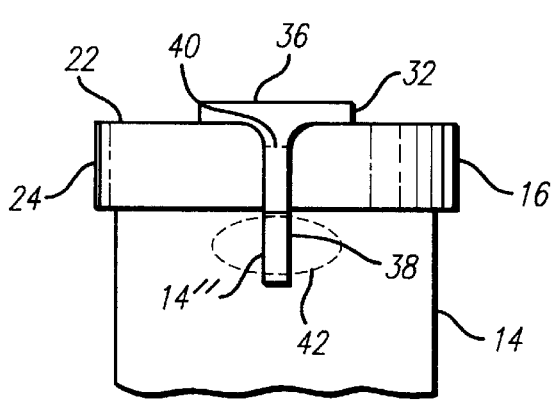
FIG. 3 is a side view of the embodiment shown in FIG. 1 taken along the line 3—3 of FIG. 1; and, FIG. 4 is a plan view of a flexible tab useful in the practice of the present invention

In those embodiments of the present invention wherein it is necessary to provide the positive indication that the lid portion 16 has not been removed from the cup portion 14, a further stamp or sealing wax or the like may be placed over the second section 38 of the flexible tab 32 and the adjacent portions of the side wall 14' of the cup portion 14 as indicated at 42 on FIG. 3.

In those embodiments of the present invention wherein it is not required to provide a positive indication that the lid porion 16 has not been removed from the cup porion 14, and the second section 38 of the flexible tab 32 is coated with the same pressure sensitive detachable adhesive as applied to the first section 36, the entire flexible tab 32 may be removed when it is desired to access the urine contained in the cup 12 and then reinstalled after each test has been performed.

The flexible tab 32 may be installed on the lid portion 16 in regions over the aperture 30 before the lid portion 16 is attached to the cup portion 14. Such an arrangement eliminates the requirement that there be maintained a separate inventory of the flexible tabs 32. The entire assembly of the flexible tab 32 installed on the lid portion 16 and the lid portion 16 installed on the cup portion 14 but without the second section 38 of the flexible tab pressed onto the side wall 14' of the cup portion 14 may be provided as a unit to facilitate supply and maintain sterility of the assembly. The lid portion 16 may be removed from the cup portion 14 when it is desired to place the urine specimen in the cup 12. After the urine specimen is in the cup portion 14, the lid portion 16 may be installed and the second section of the flexible tab 32 pressed into place on the cup portion 14.

The second section 38 of the flexible tab 32 may be utilized, in those embodiments wherein it is not permanently adhered to the top portion 16 and cup portion 14 to facilitate removal of the flexible tab when it is desired to access the contents of the cup 12 through the aperture 30.

This concludes the description of the present invention. As described above there is provided a urine specimen cup arrangement which minimizes the chance of the spilling or splashing of urine onto the test personnel during the testing of the urine specimen and which, if desired, can provide a positive indication that the lid has not been removed at any time from the cup after the urine specimen has been placed therein those skilled in the art may find many variations and adaptations of the present invention and the following claims are intended to cover all such variations and adaptations.

What is claimed is:

1. An improved urine specimen cup arrangement comprising, in combination:
    a cup portion having an open top, a closed bottom and side walls extending between said open top and said closed bottom and defining a urine containing cavity therebetween;
    a lid portion detachable connectable in sealing relationship to said open top of said cup portion and said lid portion having:
        a top section and a rim section, and said rim section enclosing said open top of said cup portion and extending a preselected distance towards said bottom of said cup portion;
        said top section having walls defining an aperture therethrough communicating with said urine containing cavity of said cup portion;
    a flexible tab having:
        a first section and a second section, and an underside for accepting adhesive thereon;
        a coating of pressure sensitive adhesive on said underside of said flexible tab;
        said first section of said flexible tab detachably mountable on said top section of said lid portion in regions adjacent said aperture to provide a detachable seal over said aperture; and
        said second section of said flexible tab engageable with said rim section of said lid portion and said side walls of said cup portion in regions adjacent said second section of said flexible tab to provide a sealing relationship therebetween.

2. The arrangement defined in claim 1 wherein:
said sealing relationship between said side walls of said cup portion and said second section of said flexible tab is a detachable sealing relationship.

3. The arrangement defined in claim 2 wherein:
said first section of said flexible tab has a coating of a pressures sensitive detachable adhesive thereon for providing said detachable sealing to said top section of said lid portion; and,
said second section of said flexible tab has a coating of a pressure sensitive detachable adhesive thereon for providing a detachable sealing relationship between said second section of said flexible tab and said side walls of said cup portion.

4. The arrangement defined in claim 3 wherein:
said flexible tab is a thin plastic sheet having a thickness on the order of 0.1 mm to 0.4 mm.

5. The arrangement defined in claim 1 wherein:
said sealing relationship between said side walls of said cup portion and said second section of said flexible tab is a permanent sealing relationship.

6. The arrangement defined in claim 5 wherein:
said flexible tab has a tear line between said first section and said second section for severing said first section from said second section to allow the removal and re-attachment of said first section from said top section of said lid portion.

7. The arrangement defined in claim 6 wherein:
said aperture in said lid portion is adjacent said rim section of said lid portion.

8. The arrangement defined in claim 7 wherein:
said first section of said flexible tab has a coating of a pressures sensitive detachable adhesive thereon for providing said detachable sealing to said top section of said lid portion; and, said second section of said flexible tab has a coating of a pressure sensitive permanent adhesive thereon for providing a permanent sealing relationship between said second section of said flexible tab and said side walls of said cup portion.

9. The arrangement defined in claim 8 wherein:

said flexible tab is a thin plastic sheet having a thickness on the order of 0.1 mm to 0.4 mm.

10. The arrangement defined in claim 1 wherein:

said first section of said flexible tab has a coating of a first pressure sensitive adhesive on a first surface thereof; and, said second section of said flexible tab has a coating of a second pressure sensitive adhesive thereon.

11. The arrangement defined in claim 10 wherein:

said first pressure sensitive adhesive coating is the same as said second pressure sensitive adhesive coating.

12. The arrangement defined in claim 10 wherein:

said first pressure sensitive adhesive coating is different from said second pressure sensitive adhesive coating.

13. The arrangement defined in claim 12 wherein:

said first pressure sensitive adhesive coating is a detachable adhesive and said second pressure sensitive adhesive coating is a permanent adhesive.

* * * * *